(12) United States Patent
Strous et al.

(10) Patent No.: US 8,034,786 B2
(45) Date of Patent: *Oct. 11, 2011

(54) METHODS AND MEANS FOR CONTROLLING THE ENDOCYTOSIS AND SUBSEQUENT DEGRADATION OF GROWTH HORMONE RECEPTOR

(75) Inventors: Gerardus Jacobus Antonius Maria Strous, Haaften (NL); Petrus Johannes Maria Van Kerkhof, Beneden Leeuwen (NL)

(73) Assignee: Recharge B.V., Bussum (NL)

( * ) Notice: Subject to any disclaimer, the term of this patent is extended or adjusted under 35 U.S.C. 154(b) by 641 days.

This patent is subject to a terminal disclaimer.

(21) Appl. No.: 11/989,995

(22) PCT Filed: Aug. 2, 2006

(86) PCT No.: PCT/NL2006/000396
§ 371 (c)(1),
(2), (4) Date: Apr. 1, 2008

(87) PCT Pub. No.: WO2007/015638
PCT Pub. Date: Feb. 8, 2007

(65) Prior Publication Data
US 2009/0156479 A1    Jun. 18, 2009

(30) Foreign Application Priority Data
Aug. 2, 2005    (EP) .................................... 05076807

(51) Int. Cl.
C12N 15/11    (2006.01)
A61K 38/08    (2006.01)

(52) U.S. Cl. ..................... 514/21.6; 514/44 A; 530/300; 530/350

(58) Field of Classification Search ......................... None
See application file for complete search history.

(56) References Cited

U.S. PATENT DOCUMENTS
6,855,546 B1 * 2/2005 Strous et al.

FOREIGN PATENT DOCUMENTS
WO    WO 99/46298        9/1999
WO    WO 2007/015638 A2  2/2007

OTHER PUBLICATIONS

Kipreos et al., Protein family review: The F-box protein family, Genome Biology 1(5):reviews 3002.1-3002.7, Nov. 10, 2000.*
van Kerkhof et al., The ubiquitin ligase SCF(betaTrCP) regulates the degradation of the growth hormone receptor, J. Biol. Chem. 282(28): 20475-20483.*

Ho, M-W, Controversy over gene therapy 'breakthrough', ISIS Report online, Institute of Science in Society, May 4, 2005.*
Zhou et al., Harnessing the ubiquitinatoin machinery to target the degradation of specific cellular proteins, Mol. Cell, 6(3):751-756, Sep. 2000.*
Dupré et al., Ubiquitin and endocytic internalization in yeast and animal cells, Biochem. Biophys. Acta, 1695:89-111, 2004.*
Kumar et al., SCFHOS ubiquitin ligase mediates the ligand-induced down-regulation of the interferon-alpha receptor, EMBO J. 22(20):5480-5490, 2003.*
van Kerkhof et al., The ubiquitin ligase SCF(betaTrCP) regulates the degradation of growth factor hormone receptor, J. Biol. Chem. 282(28):20475-20483, Jul. 13, 2007.*
Check et al., RNA to the rescue? Nature, 425:10-12, Sep. 4, 2003.*
Van Kerkhof et al., Endocytosis and degradation of the growth hormone receptor are proteasome-dependent, Journal of Biological Chemistry, Jan. 21, 2000, pp. 1575-1580, vol. 275, No. 3, American Society of Biochemistry and Molecular Biology, Inc., Birmingham, USA.
Strous et al., Abstract, Dimerization, ubiquitylation and endocytosis go together in growth hormone receptor function, FEBS Letters, Oct. 2, 2002, pp. 102-109, vol. 529, No. 1, Elsevier, Amsterdam, The Netherlands.
Van Kerkhof et al., The ubiquitin-proteasome pathway regulates the availability of the GH receptor, Endocrinology, Apr. 2002, pp. 1243-1252, vol. 143, No. 4., Baltimore, MD, USA.
Schantl et al., Small glutamine-rich tetratricopeptide repeat-containing protein (SGT) interacts with the ubiquitin-dependent endocytosis (UbE) motif of the growth hormone receptor, Biochemical Journal, Aug. 1, 2003, pp. 855-863, vol. 373, No. 3.
Van Kerkhof et al., Abstract, A method to increase the number of growth hormone receptors at the surface of cells, Molecular and Cellular Endocrinology, Mar. 28, 2003, pp. 57-62, vol. 201, No. 1-2.
Dupre et al., Abstract, Ubiquitin and endocytic internalization in yeast and animal cells, Biochimica et Biophysica Acta, Nov. 29, 2004, pp. 89-111, vol. 1695, No. 1-3.
Glickman et al., The ubiquitin-proteasome proteolytic pathway: Destruction for the sake of construction, Physiological Reviews, American Physiological Society, 2002, pp. 373-428, vol. 82, No. 2, USA.
PCT International Search Report, PCT/NL2006/000396, dated Feb. 13, 2007.

* cited by examiner

Primary Examiner — Lorraine Spector
Assistant Examiner — Claire Kaufman
(74) Attorney, Agent, or Firm — TraskBritt, P.C.

(57) ABSTRACT

The invention relates to the field of regulating metabolic processes, for example, to regulate the presence and/or activity of a receptor at the surface of a cell. The invention provides a method for controlling the presence of a receptor at the surface of a cell comprising interfering with the interaction of an F-box protein with a ubiquitin/proteasome binding site of the receptor, wherein the ubiquitin/proteasome binding site comprises particular amino acid sequences. The invention further provides a method for controlling the presence of a growth hormone receptor (GHR) at the surface of a cell comprising interfering with the interaction of an F-box protein with a ubiquitin/proteasome binding site of the GHR.

5 Claims, 3 Drawing Sheets

N-terminus
MDPAEAVLQEKALKFMCSMPRSLWLGCSSLADSMPSLRCLYNPGTGALTAFQNSSEREDCNNGEPPRKI
IPEKNSLRQTYNSCARLCLNQETVCLASTAMKTENCVAKTKLANGTSSMIVPKQRKLSASYEKEKELCV
KYFEQWSESDQVEFVEHLISQMCHYQHGHINSYLKPMLQRDFITALPARGLDHIAENILSYLDAKSLCA
AELVCKEWYRVTSDGMLWKKLIERMVRTDSLWRGLAERRGWGQYLFKNKPPDGNAPPNSFYRALYPKII
QDIETIESNWRCGRHSLQRIHCRSETSKGVYCLQYDDQKIVSGLRDNTIKIWDKNTLECKRILTGHTGS
VLCLQYDERVIITGSSDSTVRVWDVNTGEMLNTLIHHCEAVLHLRFNNGMMVTCSKDRSIAVWDMASPT
DITLRRVLVGHRAAVNVVDFDDKYIVSASGDRTIKVWNTSTCEFVRTLNGHKRGIACLQYRDRLVVSGS
SDNTIRLWDIECGACLRVLEGHEELVRCIRFDNKRIVSGAYDGKIKVWDLVAALDPRAPAGTLCLRTLV
EHSGRVFRLQFDEFQIVSSSHDDTILIWDFLNDPAAQAEPPRSPSRTYTYISR
C-terminus

METHODS AND MEANS FOR CONTROLLING THE ENDOCYTOSIS AND SUBSEQUENT DEGRADATION OF GROWTH HORMONE RECEPTOR

CROSS-REFERENCE TO RELATED APPLICATIONS

This is a national phase entry under 35 U.S.C. §371 of International Patent Application PCT/NL2006/000396, filed Aug. 2, 2006, published in English as International Patent Publication WO 2007/015638 A2 on Feb. 8, 2007, which claims the benefit under 35 U.S.C. §119 of International Patent Application EP 05076807.6, filed Aug. 2, 2005.

TECHNICAL FIELD

The invention relates to the field of regulating metabolic processes and, more particularly, regulating the presence and/or activity of a receptor at the surface of a cell.

BACKGROUND

A receptor (protein) on the surface of a cell has a binding site with, typically, a high affinity for a particular signalling substance (a hormone, pheromone, neurotransmitter, etc.). The specific signalling substance is often referred to as the ligand, a substance that binds to or fits in a site, the ligand binding site. When the signalling substance binds to a receptor, a receptor-ligand complex initiates a sequence or cascade of reactions that changes the function of the cell. A cell surface receptor polypeptide typically comprises an extracellular part that comprises a binding site where the ligand can interact, a transmembrane part that locates a receptor in the cell membrane, and an intracellular part that plays a role in transducing a signal further into the cell once a ligand has bound. A receptor polypeptide can span the cell membrane several times resulting in multiple extra- and intracellular domains.

The response of a cell or tissue to, for example, specific hormones is dictated by the particular receptors it possesses and by the intra- or inter-cellular reactions initiated by the binding of any one hormone to its receptor.

One cell may have two or more types of receptors or various cell types may have different sets of receptors for the same ligand, each of which induces a different response. Alternatively, the same receptor may occur on various cell types, and binding of the same ligand may trigger a different response in each type of cells. Clearly, different cells respond in a variety of ways to the same ligand, depending on a receptor or its interaction with the cell.

A wide variety of receptors specific for a wealth of ligands exist. Examples can be found among ion-channels, such as $Ca^+$ channels, or $Cl^-$ channels or $Na^+$ channels, glucose transporters; among immunoglobulin receptors, such as IgE receptors; among cytokine receptors; among multi-drug transporters, and so on. Receptors, as defined herein, relate to signal-transducing molecules in the broadest sense. These signal-transducing molecules include ion pump-like proteins, for example, the above-mentioned ion channels that transport the ligand (here the ion) through the membrane include receptors that bind to a ligand (eliciting a signal over the membrane) but that do not transport the ligand itself through the membrane, include transport proteins and include enzymes that act upon contact with a substrate. As an example, receptors having as ligand a hormone are herein discussed in more detail, however, physiological mechanisms regulating hormone receptor availability and signal transduction are also found among a large variety of receptors having another ligand. As a non-limiting example, the growth hormone receptor is, further below, described in even more detail.

Hormones reacting with cell surface receptors are of a varied nature. Typical examples are amino acid derivatives such as epinephrine or histamine, prostaglandins, various peptide hormones such as glucagon, insulin, gastrin, secretin, ACTH, LH, FSH, TSH, TRH, LHRH, vasopressin, IGF-I or IGF-II, EGF, somatotropin (growth hormone), prolactin, erythropoietin, EGF, and others.

These hormones all act by binding to their specific surface receptor, after which their specific signal is being transduced, directly or by an intracellular signalling substance (a second messenger), leading to the specific action that is required of the cell.

The amount of functional (hormone) receptor on the cell surface is not constant. A receptor level is modulated up (up-regulation) or down (down-regulation), permitting the cell to respond to small changes in the hormone (ligand) level. The number of cell surface receptors is often down-regulated by endocytosis, whereby the sensitivity of the cell for the specific hormone (ligand) is reduced.

In general, when a ligand (hormone) binds to its receptor and results in a ligand-receptor complex, two phenomena occur. On the one hand, the signal transduction cascade is initiated while, on the other hand, the ligand-receptor complexes are brought in the cell by receptor-mediated endocytosis and the internalised ligand (hormone) is degraded. Internalisation and degradation most likely terminate the hormone signal.

Some receptors recycle to the cell surface by exocytosis; however, even if they do, often a substantial fraction will be in the internal membrane compartments at any one time. Fewer receptors will be on the cell surface, available to bind extracellular hormone. Other receptors get degraded by proteolytic cleavage processes in the cell and, thus, do not or only insignificantly recycle to the cell surface, again reducing the number of available receptors on the cell surface.

Another way by which receptor availability on the cell surface is down-regulated is by removal, for example, by specific proteolysis of the extra-cellular part that comprises parts of the binding site of a receptor. Such removal is in essence a physiological mechanism that serves to refresh the available receptors and replace them with new ones; however, it again is a factor in reducing receptor availability.

As a consequence of fewer functional receptors being available on the cell surface, the hormone concentration necessary to induce the physiological response is higher and the sensitivity of the cell to the hormone is reduced. The susceptibility of a cell or tissue to the action of a hormone is, thus, among others dependent on the number of functional receptors present at any given time on the surface of a cell. Even when ligands are circulating at a high concentration, these cannot result in sufficient activation when not enough receptors are present.

Many hormonal related or other diseases would benefit from an up-regulation of hormone or ligand activity. In hormonal dysfunctioning, one often attempts to achieve such up-regulation simply by treating a patient with exogenous hormones; however, as explained above, such a treatment may not be effective due to the fact that the number of available surface receptors for that hormone are too low. This is often aggravated by the fact that higher hormone concentrations enhance, by feed-back mechanisms, the further down-regulation of the specific receptor. Exogenous hormone therapy may then even be counterproductive, the patient becomes less susceptible to the hormone in question.

BRIEF DESCRIPTION OF THE DRAWINGS

FIG. 1: β-TrCP silencing inhibits $^{125}$I-GH endocytosis. Hek293 cells expressing GHR were transfected with various siRNAs for three days. Cells were incubated in the presence of $^{125}$I-GH on ice and uptake was measured for 10 minutes at 37° C. The cells were acid washed (to determine GH at the plasma membrane) and the acid-resistant radioactivity was taken as endocytosed GH. Internalised GH was expressed as a percentage of total radioactivity associated with the cells. Background values were determined by performing the experiment in the presence of excess unlabelled GH and subtracted. Silencing of clathrin was used as a positive control. Silencing of other E3s (Traf2, Traf6), a ubiquitin conjugase (Ubc13), an endosomal sorting factor (TSG101), and small glutamine-rich tetratricopeptide repeat-containing protein, a known GHR binding protein, did not affect GHR endocytosis.

FIG. 2: Mutational analysis of the interaction between (β-TrCP and the GHR. Hek293 cells transfected with GHR DNA constructs in which each of the UbE amino acids were mutated to alanine were lysed, the lysates were incubated with biotin-GH, and the GHRs were isolated using Strepavidin-agarose beads. The GH-GHR-containing beads were incubated with β-TrCP1, $^{35}$S-labelled in an in vitro translation system. The beads were washed, and the amounts of radioactive β-TrCP2 bound to the beads were quantitated after separation on SDS electrophoresis. Each lane contained approximately equal amounts of GHR as quantified from the Western blot using an ODYSSEY® scanner, Biosciences, Lincoln, Nebr. The values are expressed as percentages of binding to the wild-type receptor. Binding to the GHR truncated at amino acid residue 286 was subtracted before the calculation.

DETAILED DESCRIPTION OF THE INVENTION

As already described above, the growth hormone receptor is described in more detail to exemplify the present invention.

Cells of the human body contain growth hormone receptors (GHR). Upon growth hormone (GH) binding, these receptors initiate signal transduction that results in the expression of genes that are involved in anabolic processes: protein synthesis, lipid degradation, etc. At the cell surface, the expression of GHR is controlled by two major factors: (i) endocytosis and (ii) proteolytic cleavage of the extra cellular domain. In the first process, the clathrin-mediated endocytosis of the GHR depends on the activity of the ubiquitin system, and the second factor is the activity of TACE, tumour necrosis factor-α-converting enzyme, also referred to as Adam 17. Together, they largely determine the residence time of the GHR at the cell surface. Inhibition of both activities prolongs the half-life of the GHR from less than one hour to several hours. Inhibition of the ubiquitination-dependent endocytosis results in a two- to three-fold increase of GHRs at the cell surface (van Kerkhof et al., 2003).

A specific motif in the GHR cytoplasmic tail regulates receptor endocytosis via the ubiquitin-conjugation system. This motif, the Ubiquitin-dependent Endocytosis motif (UbE motif), consists of the amino acid sequence DDSWVEFIELD (SEQ ID NO:1) (Govers et al., 1999). Mutational analysis of this motif has shown that the bolded and underlined amino acid residues are important for endocytosis and consequent degradation of the GHR in lysosomes. If these amino acid residues are mutated to alanine, endocytosis of the GHR dramatically drops, rendering the cells more GH sensitive. This finding was described in patent application WO 99/46298.

The ubiquitin-proteasome degradation pathway provides the major pathway for non-lysosomal degradation (reviewed in Hershko et al., 2000). It is involved in the degradation of cytoplasmic proteins and proteins, which do not pass the quality control of the ER, and plays a role in regulating a variety of cellular functions (Plemper and Wolf, 1999). Covalent attachment of the 76-amino acid peptide ubiquitin to substrate proteins is a highly conserved process that occurs via the sequential action of three enzymes: the ubiquitin-activating enzyme E1, a ubiquitin conjugase E2, and a ubiquitin ligase E3.

E3s are either single proteins or multiprotein complexes. Two major classes exist: HECT E3s form a thioester bond with ubiquitin within the HECT domain during the transfer of ubiquitin from the E2 to the substrate, RING domain E3s have no intrinsic catalytic activity, but they coordinate the ubiquitin transfer by binding E2, serving as a scaffold. RING E3s consist of two subclasses: single peptide E3s (e.g., c-Cb1, Mdm2, Traf), and RING E3 complexes in which the substrate-recognition site and RING domain are in different proteins (e.g., SCF E3s). In SCF (Skp1/Cullin/F-box) complexes, the F-box protein plays the role of recruiting on one site the cognate adapter protein and the rest of the E3 complex via its F-box motif of about 40 amino acids on the other site the substrate.

Beta-transducing repeat-containing proteins (β-TrCP) serve as the substrate recognition subunits for the SCF$^{TrCP}$ ligases. Beta-TrCP exists in two isoforms: β-TrCP1 and β-TrCP2. Beta-TrCP1 has two variants: β-TrCP1 variant 1 and β-TrCP1 variant 2. Beta-TrCP2 has three variants: β-TrCP2 variant 1, β-TrCP2 variant 2 and β-TrCP2 variant 3. Variant 1 from β-TrCP1 has an additional insert of 36 amino acids as compared to variant 2 from β-TrCP1 (see underlined part in FIG. 3). These ligases play a role in cell division and various signal transduction pathways essential for many aspects of tumorigenesis. Their substrate binding motifs consist of seven propeller-shaped WD40 domains that specifically bind short motifs in its central cavity. Examples of substrates are β-catenin, NFκB, and inhibitor of NFκB. These motifs generally are six amino acid residues long with a common structure of $DSG(X)_{2+n}S$ (SEQ ID NO:2). To be recognised by the SCF E3, both serine residues need to be phosphorylated; in some instances, recognition may also occur if the phosphorylated serines are replaced by an acidic amino acid residue. Recognition by SCF E3s results in polyubiquitination and degradation by the proteasome. In some cases, the substrate is only partially degraded resulting in active (transcription) factors like NFκB.

Recently, it became evident that for a restricted number of plasma membrane proteins, ubiquitination triggers internalisation and vacuolar/lysosomal rather than proteasomal degradation (reviewed in Strous and Govers, 1999). This pathway is best understood in yeast, where a number of plasma membrane proteins is endocytosed in a ubiquitin-dependent manner (Galan and Haguenauer-Tsapis, 1997; Hicke and Dunn, 2003; Terrell et al., 1998). Several studies showed that mono-ubiquitination of proteins is sufficient to stimulate their endocytosis (Galan and Haguenauer-Tsapis, 1997; Roth and Davis, 2000; Terrell et al., 1998). In mammalian cells, the GHR, the β-adrenergic receptor, and the epithelial sodium channel, ENaC, are cell surface proteins known to be endocytosed ubiquitin system-dependent (Shenoy et al., 2001; Staub et al., 1997; Strous and Gent, 2002). Ubiquitination of β-arrestin by the E3 Mdm2 is required for endocytosis of the β2-adrenergic receptor, suggesting that the ubiquitination of an adaptor protein triggers endocytosis (Shenoy et al., 2001).

Recently, it became clear that the DSG(X)$_{2+n}$S (SEQ ID NO:2) motif in some cytokine receptors serves as a degradation signal via the SCF(β-TrCP) ligases. Both for the interferon-α and for the prolactin receptor, it was shown that this E3 is involved in their degradation. An important finding in these studies was that receptor degradation mainly depends on ligand binding (interferon-α, prolactin, respectively); in addition, phosphorylation at both serine residues was required. This renders yet unidentified kinases the controlling factors for interferon/prolactin receptor degradation (Kumar et al., 2003; Kumar et al., 2004; Li et al., 2004).

β-TrCP is a factor in the degradation of prolactin and interferon receptors (Kumar et al., 2003; Kumar et al., 2004; Li et al., 2004). Fuchs et al. identified β-TrCP to act upon and interact with these receptors via their DSGΦXS destruction motifs. They also show that SCF(β-TrCP2) E3 ubiquitinates both the interferon-α and prolactin receptors, dependent on an intact DSGΦXS motif. The assumption is that upon ligand binding (interferon-α and prolactin), this motif is phosphorylated by a yet unidentified kinase after which the SCF(β-TrCP2) E3 ubiquitinates certain lysines in the tail of the receptors.

Although the growth hormone receptor (GHR) comprises a DSGΦXS destruction motif, it is now surprisingly disclosed that a completely different motif plays a role in the ubiquitin-mediated proteolysis of a GHR. Moreover, it is also shown that β-TrCP is involved in the endocytosis of the GHR.

This finding led us to develop, among others, pharmacological tools or medication that can up- or down-regulate the presence of signal transduction of ligand-specific proteins such as transport proteins, enzymes, cytosolic receptors or receptors on the surface of cells, for example, to help a patient to better respond to hormonal therapy or to provide the cells of the patient with a higher sensitivity to an endogenous hormone or other ligand.

In a first embodiment, the invention provides a method for controlling the presence of a receptor at the surface of a cell comprising interfering with the interaction of an F-box protein with a ubiquitin/proteasome binding site of the receptor, wherein the ubiquitin/proteasome binding site comprises the amino acid sequence motif xDSWxEFIxxD (SEQ ID NO:3) or a sequence essentially corresponding thereto (such as DxSWxEFIxxD (SEQ ID NO:4) or DDSWxEFIxxD (SEQ ID NO:5)). It is now disclosed for the first time that an F-box protein is capable of interacting with (the intracellular part of) a receptor, not only via a so-called DSGΦXS destruction motif, but also via the UbE motif or a sequence essentially corresponding thereto. This was highly unexpected because the prolactin receptor, which comprises a UbE motif as well as a DSGΦXS destruction motif, is reported to be controlled via the DSGΦXS destruction motif. The GHR also comprises a UbE motif as well as a DSGΦXS destruction motif, but its presence at the surface of the cell is (as shown herein) (at least partly) controlled by an interaction between an F-box protein and the UbE-motif. Although we now have shown that the interaction of an F-box protein and the UbE motif plays a role in the amount of receptor present at the cell surface, it is not to be excluded that any other sequence parts of the receptor may also play a role in the proteolysis of a receptor in general and of GHR in particular. For example, sequences present between the UbE motif of GHR and the transmembrane domain of GHR might play a(n) (additional) role. However, we have herein shown that some mutations of the UbE motif already lead to background signals.

Depending on the specific aim of a method according to the invention, the controlling step is to be understood as to result in either a decrease of the amount of receptor molecules present at the surface of a cell or to result in an increase of the amount of receptor molecules present at the surface of a cell or to result in a more or less constant/stable amount of receptor molecules.

Whether or not a receptor is present at the surface of a cell can be determined in different ways. The presence of a receptor at the surface of a cell is, for example, determined with the help of antibodies (specifically) directed to the receptor or by binding studies using, for example, fluorescently or radioactively labelled GH.

Preferably, before a method of the present invention is applied, the amount of receptors at the surface of a cell is determined. This process is repeated after the interfering step. The amount of receptors before and after the interfering step is then compared and it is determined whether the desired controlling (up- or down-regulation) has succeeded.

Whether the controlling step results in an increased/decreased more or less constant amount (or level) of receptors at the surface of a cell is accomplished by interfering with the interaction of an F-box protein with a ubiquitin/proteasome binding site of the receptor. To decrease the amount of receptors present at the surface of a cell, the interaction is at least partly increased.

In a preferred embodiment, the amount of receptors present at the cell surface is increased. This is accomplished by at least in part decreasing the interaction between an F-box protein with a ubiquitin/proteasome binding site (preferably the UbE motif) of the receptor. "At least in part" is defined herein such that the interaction between an F-box protein and a ubiquitin/proteasome binding site is disturbed to such an extent that the presence of a receptor at the surface is (preferably significantly) increased. More preferably, interaction is completely inhibited and, hence, the presence of a receptor at the surface of a cell is (preferably significantly) increased, which renders the cell more sensitive to the corresponding ligand (GH in the case of the GHR). The invention, therefore, provides a method for increasing the presence of a receptor at the surface of a cell comprising providing to the cell an inhibitor that at least in part is capable of inhibiting the interaction of an F-box protein with a ubiquitin/proteasome binding site of the receptor, wherein the binding site comprises the amino acid sequence motif xDSWxEFIxxD (SEQ ID NO:3) or a sequence essentially corresponding thereto.

Preferably, the inhibition of the interaction between the F-box protein and the ubiquitin/proteasome binding site (preferably the UbE motif) is such that only the amount of one particular receptor (preferably GHR) is changed without changing the amount of other receptor molecules or without interfering with the action of other molecules such as catenin, NFκB and the inhibitor of NFκB, the inhibitor of APC Emi1, the Cdc2 inhibitory kinase Wee1, the transcription repressor Per-1, the transcription factor ATF4, and Cdc25B Phosphatase active at G2/M transition, i.e., the inhibitor preferably specifically interferes with the binding of the F-box protein and UbE binding site of the to be modified (for example, increased) receptor.

Preferably, the ubiquitin/proteasome binding site comprises the amino acid sequence motif xDSWxEFIxxD (SEQ ID NO:3) or a sequence essentially corresponding thereto, which sequence is found in the intra-cellular polypeptide part of the receptor.

The herein-used nomenclature for amino acid residues corresponds with the internationally accepted nomenclature and, hence, D is the amino acid aspartic acid, E is the amino acid glutamic acid, F is the amino acid phenylalanine, I is the amino acid isoleucine, S is the amino acid serine, W is the amino acid tryptophan and X is any other amino acid.

"Essentially corresponding" means herein that the amino acid motif relates to a variety of specific amino acid sequences. For example, the amino acid E (glutamic acid) in the motif can be replaced by the like amino acid D (aspartic acid), F (phenylalanine) can be replaced by Y (tyrosine), I (isoleucine) by L (leucine), V (valine) or F (phenylalanine), S (serine) by T (threonine), or D by E. A further detailed example is the amino acid sequence DxSWxEFIxxD (SEQ ID NO:4) or DDSWxEFIxxD (SEQ ID NO:5) or DDSWVEFIELD (SEQ ID NO:1) or DDSWVEFIELDI (SEQ ID NO:6) (the last two examples located, for example, at a distance of about 50 amino acid residues from the plasma membrane in the intracellular part of the growth hormone receptor).

Previously, we have shown that endocytosis of the GHR depends both on a functional ubiquitination system and on an intact UbE motif (Govers et al., 1997; Strous et al., 1996; van Kerkhof et al., 2002). Using mutational analysis of the UbE motif by changing every single amino acid residue into alanine, the contribution of each amino acid was determined. The experiment showed that mutation of some of the residues, indicated in bold (and underlined) in the UbE motif (DDSWV EFIELD) (SEQ ID NO:1) almost completely inhibited endocytosis.

Figure 2:
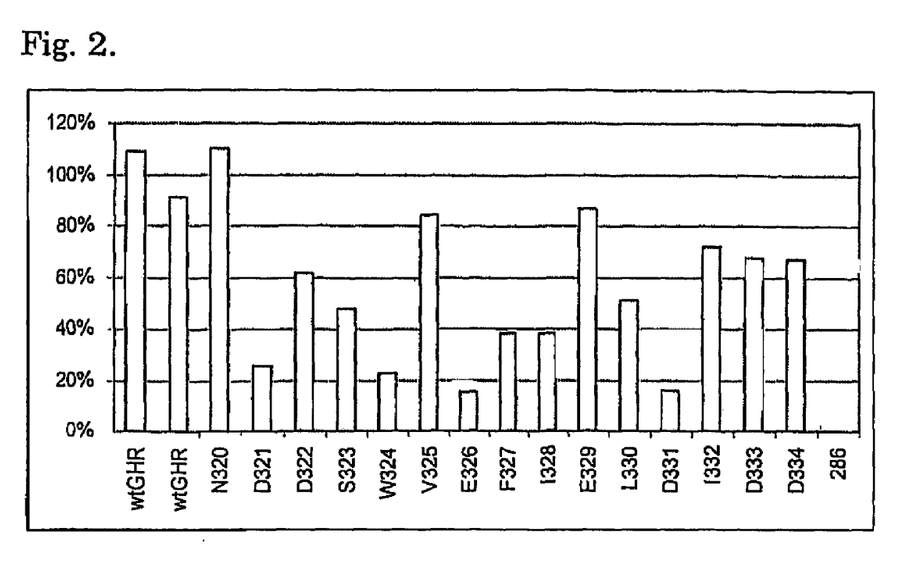

We now used a pull-down assay to determine whether β-TrCP binds to the GHR. Hek293 cells were transfected with 15 GHR constructs in which each of the amino acids of the UbE motif were changed into alanine (NDDSWVEFIELD-IDD (SEQ ID NO:7), 320-334). After 24 hours, GHRs were isolated using biotinylated GH and incubated with equal amounts of β-TrCP, $^{35}$S-labelled in an in vitro transcription-translation system. The bound radioactivity was analysed by electrophoresis on SDS gels and quantitated. As a control, DNA encoding wild-type GHR (FIG. 2, wtGHR) was used, and as a negative control, DNA encoding GHR truncated at amino acid 286 (FIG. 2, 286), lacking the UbE motif was used. The results show that except for the N320A, every mutation resulted in inhibition of β-TrCP binding as compared to wtGHR. However, mutation of seven amino acids inhibited the β-TrCP binding with more than 60% indicated as underlined (DDSWVEFIELD) (SEQ ID NO:1), while the greatest effects were observed if either one of three acidic amino acid residues (D321, E326, D331) or S323, or W324 were mutated into alanine. The latter effects approximated the background signal measured for the GHR truncated at amino acid 286.

Therefore, in a preferred embodiment, the invention provides a method for controlling the presence of a receptor at the surface of a cell comprising interfering with the interaction of an F-box protein with a ubiquitin/proteasome binding site (preferably the UbE motif) of the receptor or a method for increasing the presence of a receptor at the surface of a cell comprising providing to the cell an inhibitor that at least in part is capable of inhibiting the interaction of an F-box protein with a ubiquitin/proteasome binding site (preferably the UbE motif) of the receptor, wherein the ubiquitin/proteasome binding site comprises the amino acid sequence motif DxSWxEFIxxD (SEQ ID NO:4) or a sequence essentially corresponding thereto, such as the amino acid sequence motif DDSWxEFIxxD (SEQ ID NO:5) or the amino acid sequence motif DDSWVEFIELD (SEQ ID NO:1).

We now disclose that the UbE motif in the GHR tail is specifically recognised by β-TrCP and, hence, in a preferred embodiment, the mentioned F-box protein is a β-transducing repeat-containing protein (β-TrCP). In a more preferred embodiment, the β-TrCP is β-TrCP1 and, in an even more preferred embodiment, the β-TrCP1 is β-TrCP1 variant 1 with the 36 extra amino acids (FIG. 3) to increase the specificity and functionality toward the degradation of the growth hormone receptor. Even more preferably, the to-be-controlled receptor is a growth hormone receptor (GHR).

A method according to the invention can be performed in vitro as well as in vivo. The in vitro method is, for example, extremely useful for the testing of compounds that are possible inhibitors of the interaction between an F-box protein and a ubiquitin/proteasome binding site of a to-be-controlled receptor. The in vivo method is, for example, useful in helping a patient to better respond to hormonal therapy or to provide the cells of the patient with a higher sensitivity to an endogenous hormone or other ligand.

The inhibitor used in a method according to the invention can be a peptide or peptide analogue or mimetica that is derived from, competes with, or binds to any of the above-mentioned ubiquitin/proteasome binding sites. We have determined that, for example, a peptide consisting of the amino acids 270-331 (61 amino acids) of GHR is capable of providing inhibition. The sequence of human 61 amino acid peptide is:

270-KQQRIKMLILPPVPVPKIKGIDP-
DLLKEGKLEEVNTILAIHDSYKPEFHSDDS WVE-
FIELD-331 (SEQ ID NO:8), and the sequence of the rabbit 61 amino acid sequence is:

270-KQQRIKMLILPPVPVPKIKGIDP-
DLLKEGKLEEVNTILAIQDSYKPEFYNDDS WVE-
FIELD-331 (SEQ ID NO:9).

A person skilled in the art is very well capable of making smaller peptides or derivatives based on the sequence of this 61 amino acid peptide of GHR. Such peptides are also part of the invention. Such a smaller peptide comprises between five and fifty amino acids or five and forty amino acids or five and thirty amino acids, preferably between five and twenty amino acids, more preferably between five and ten amino acids and most preferably between five and fifteen amino acids. Methods to test such peptides for their capability to inhibit the interaction between, for example, the GHR and β-TrCP are provided herein.

Such a peptide, peptide analogue or mimetica is preferably provided with a means for transport across the cell membrane. A non-limiting example is the HIV-TAT domain. A peptide or peptide analogue or mimetica that is derived from the ubiquitin/proteasome binding site (xDSWxEFIxxD (SEQ ID NO:3) or DxSWxEFIxxD (SEQ ID NO:4) or DDSWxEFIxxD (SEQ ID NO:5) or DDSWVEFIELD (SEQ ID NO:1)) is preferably designed such that it has 70% homology with the ubiquitin/proteasome binding site, more preferably 80% homology, even more preferably 90% homology, and most preferably 95% homology.

Thus, the invention also provides a peptide or peptide analogue or mimetica derived from an amino acid sequence that corresponds to the amino acid motif xDSWxEFIxxD (SEQ ID NO:3) or DxSWxEFIxxD (SEQ ID NO:4) or DDSWxEFIxxD (SEQ ID NO:5) or DDSWVEFIELD (SEQ ID NO:1) or to a motif essentially corresponding thereto (as defined herein). A peptide that competes, binds, or interacts in another way with such an amino acid sequence is herein also considered to be derived from an amino acid sequence corresponding to such a motif. Such a peptide is selected according to methods known by a person skilled in the art. It is to be expected that the conformation of a selected peptide is important for its reactivity. Appropriate conformational changes can be introduced in selected peptides by techniques known to a person skilled in the art. For example, it is possible to introduce appropriate conformation by using disulfide bridges. In addition, other peptide sequences or compounds mimicking the wanted conformation (mimetic) can be selected by a person skilled in the art. A suitable system to select a peptide is a system such as the PEPSCAN system, whereby interaction, such as competition or inhibition, is measured against sets of overlapping peptides chosen from the receptor's amino acid sequence. Peptide analogues, whereby specific amino acids are replaced by others, being either L- or D-amino acids, are tested similarly. Other methods include replacement scanning of selected peptide sequences, for example, by replacing distinct amino acids by alanine, whereby crucial amino acids in the selected peptides are determined. Peptides can be made synthetically or via recombinant techniques.

In yet another embodiment, the inhibitor is a small (chemical) compound that is, for example, obtained from a small compound library. Methods to identify such compounds will be discussed in more detail below.

In another embodiment, the inhibitor is derived from an antibody (or more preferably, a part thereof) directed against the ubiquitin/proteasome binding site or directed to the part of the β-TrCP that interacts with the UbE motif. It is clear to a person skilled in the art that, preferably, the antibody (or a part thereof) is directed against the ubiquitin/proteasome binding site, to avoid any undesired side effects by interfering with the other functions of an F-box protein. A person skilled in the art is very well aware of the way in which antibodies (or parts thereof) can be raised and, hence, no further discussion is needed on this matter. Preferably, the raised antibodies are monoclonal antibodies. Antibodies, or a part thereof, can further be provided with a means that facilitate transport across the cell membrane (for example, the HIV TAT domain). A non-limiting example of a useful part of an antibody is the CDR3 region of the heavy chain, which specifically interacts with at least part of the ubiquitin/proteasome binding site or which is capable of binding to a dimerised ubiquitin/proteasome binding site.

In yet another preferred embodiment, the inhibitor is a compound that binds (more or less) irreversibly to the UbE motif (or a sequence essentially corresponding thereto). Such an inhibitor has overall basic characteristics and is capable of forming hydrophobic interactions with the amino acids F and/or W of the UbE motif By (more or less) irreversibly blocking the UbE motif, the F-box protein is not able to interact with the UbE motif and, as a result, the corresponding receptor molecule will not be removed from the cell surface; this results in a prolonged presence of the receptor at the surface of a cell.

In yet another preferred embodiment, the inhibitor is a compound that is capable of cross-linking two receptor molecules approximately around the interaction site of the receptor with the F-box protein. GHR, especially, is present at the cell surface in a dimerised form (in the presence, as well as in the absence, of GH). Such an inhibitor results in a conformational change in the receptor, which (at least partly) blocks the interaction with the F-box protein. Again, this results in a prolonged presence of the receptor at the cell surface.

As a general comment on the inhibitor, it is noted that preferably the action of the inhibitor does not, or at least not substantially, disrupt the capabilities of the receptor to, after ligand binding, initiate the signal transduction cascade.

Dependent on the specific type of inhibitor, the inhibitor either blocks the ubiquitin/proteasome binding site by interacting with/binding to the site such that β-TrCP can no longer functionally interact with the ubiquitin/proteasome binding site or the inhibitor (specifically) interacts with the F-box protein (β-TrCP), such that the F-box protein can no longer functionally interact with the ubiquitin/proteasome binding site/UbE motif of the receptor. In the latter situation, the inhibition is preferably specific, such that the interaction of the F-box protein with other binding sites are not, or hardly not, affected. In either case, the action of the inhibitor results in more receptors at the surface of a cell or for a prolonged presence of a certain receptor at the surface of a cell, thereby making the cell more responsive to the corresponding ligand (in the case of GHR: growth hormone).

In a second embodiment, the invention provides a method for controlling the presence of a growth hormone receptor (GHR) at the surface of a cell comprising interfering with the interaction of an F-box protein with the ubiquitin/proteasome binding site (preferably UbE motif) of the GHR. It is disclosed herein, to our knowledge for the first time, that an F-box protein is involved in endocytosis of the GHR by interacting with such a binding site of the GHR. Based on this finding, the amount of GHR can now be controlled by interfering with this interaction.

Preferably, the amount of GHR at the cell surface is at least partly increased by at least partly blocking the interaction between an F-box protein and a ubiquitin/proteasome binding site of GHR with the help of an inhibitor and, hence, the invention provides a method for increasing the presence of a GHR at the surface of a cell comprising providing to the cell an inhibitor that, at least in part, is capable of inhibiting the interaction of an F-box protein with the ubiquitin/proteasome binding site/UbE motif of the GHR. More preferably, the F-box protein is a β-transducing repeat-containing protein (β-TrCP). In a more preferred embodiment, the β-TrCP is β-TrCP1 and, in an even more preferred embodiment, the β-TrCP1 is β-TrCP1 variant 1 with the 36 extra amino acids (FIG. 3) to increase the specificity and functionality toward the endocytosis and degradation of the growth hormone receptor. Even more preferably, the mentioned ubiquitin/proteasome binding site comprises the amino acid sequence motif xDSWxEFIxxD (SEQ ID NO:3), or the amino acid sequence DxSWxEFIxxD (SEQ ID NO:4), or the amino acid sequence DDSWxEFIxxD (SEQ ID NO:5), or a sequence essentially corresponding thereto (as outlined above). In an even more preferred embodiment, the invention provides a method for controlling the presence of a GHR at the surface of a cell comprising interfering with the interaction of an F-box protein with the ubiquitin/proteasome binding site/UbE motif of the GHR, wherein the ubiquitin/proteasome binding site comprises the amino acid sequence motif DDSWVEFIELD (SEQ ID NO:1), or a sequence essentially corresponding thereto.

As outlined above, such a method can be performed in vitro as well as in vivo.

In yet another embodiment, the invention provides a method for selecting an inhibitor capable of inhibiting the interaction of an F-box protein with the ubiquitin/proteasome binding site/UbE motif, comprising the steps of: contacting, in the absence or presence of a possible inhibitor, the F-box protein or a functional part and/or equivalent thereof with a first labelled compound comprising at least a proteinaceous part comprising the amino acid sequence xDSWxEFIxxD (SEQ ID NO:3) or a sequence essentially corresponding thereto; determining the amount of the first labelled compound bound to the F-box protein in the presence or absence of the inhibitor and comparing the obtained amounts; and selecting the inhibitor that results in a decreased amount of the bound first labelled compound.

Such a method is very useful in large-scale and/or high throughput screenings and, hence, allows for the screenings of libraries of possible inhibitors, for example, small (chemical) compound libraries, or peptide libraries, or libraries containing natural and organic substances/products.

The first labelled compound can be in very different forms but at least comprises a proteinaceous part. The proteinaceous part preferably comprises the amino acid sequence xDSWx-EFIxxD (SEQ ID NO:3) or a sequence essentially corresponding thereto. Examples of other useful sequences are the amino acid sequences DxSWxEFIxxD (SEQ ID NO:4) or DDSWxEFIxxD (SEQ ID NO:5) or DDSWVEFIELD (SEQ ID NO:1). The amino acid sequence may optionally be somewhat extended at the N- and/or C-terminus by, for example, two or three extra amino acids. The first labelled compound that comprises at least a proteinaceous part comprising the amino acid sequence xDSWxEFIxxD (SEQ ID NO:3) may also be the complete (optionally dimerised) GHR or the intracellular part of GHR.

The first labelled compound further comprises a label. Examples of suitable labels are fluorescent labels such as Cy3, Cy5 or Alexa-based labels or radioactively based labels.

Figure 3:
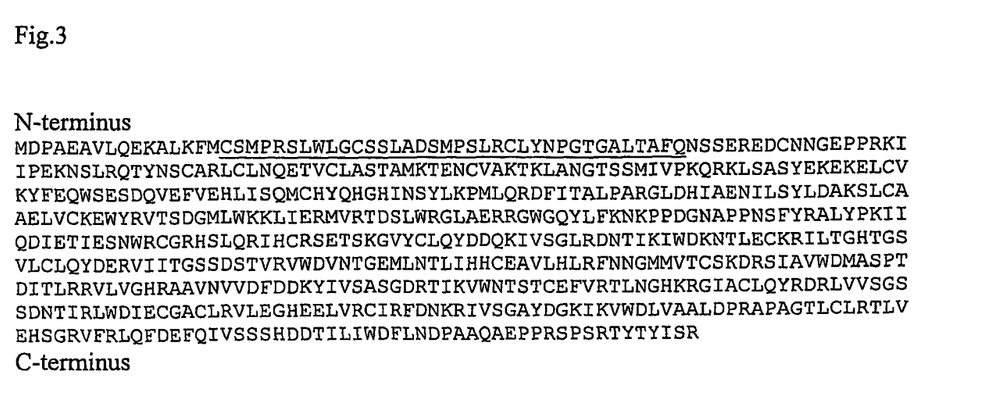
FIG. 3: The amino acid sequence of β-TrCP1 variant 1 (SEQ ID NO:13) and variant 2. Variant 1 has an additional insert of 36 amino acids (underlined).

Preferably, the F-box protein or a functional part and/or equivalent thereof is β-TrCP or a functional part and/or equivalent thereof. In a more preferred embodiment, the β-TrCP is β-TrCP1 and, in an even more preferred embodiment, the β-TrCP1 is β-TrCP1 variant 1, including the functionality of the extra 36 amino acids (FIG. 3). A functional part and/or equivalent thereof is, for example, detected by using mutations and deletions of β-TrCP. Although not described in detail in the experimental part, we have shown that the interaction between the xDSWxEFIxxD (SEQ ID NO:3) amino acid sequence and β-TrCP occurs via the WD40 domain of β-TrCP. In a more preferred embodiment, the functional part of β-TrCP comprises the WD40 domain.

In view of the first labelled compound comprising at least a proteinaceous part comprising the amino acid sequence xDSWxEFIxxD (SEQ ID NO:3) or a sequence essentially corresponding thereto and in view of the F-box protein or a functional part and/or equivalent thereof, it is clear that different combinations can be used in a method for selecting an inhibitor capable of inhibiting the interaction between an F-box protein and a ubiquitin/proteasome binding site/UbE-based motif. Non-limiting examples include (i) the use of a complete F-box protein in combination with a first labelled compound comprising only the amino acid sequence xDSWxEFIxxD (SEQ ID NO:3) (or a sequence essentially corresponding thereto), possibly extended by a limited (two or three) amount of amino acids on the N- and/or C-terminus or (ii) the use of a complete F-box protein in combination with a first labelled compound comprising essentially the complete intracellular domain of, for example, GHR or comprising essentially the complete GHR molecule or (iii) the use of a functional part and/or equivalent of an F-box protein (for example, the WD40 domain of β-TrCP), in combination with a first labelled compound comprising only the amino acid sequence xDSWxEFIxxD (SEQ ID NO:3) (or a sequence essentially corresponding thereto), possibly extended by a limited (two or three) amount of amino acids on the N- and/or C-terminus.

By comparing the amount of signal resulting from an incubation between an F-box protein (or a functional part and/or equivalent thereof) and a first labelled compound in the absence of a possible inhibitor (or in the presence of a non-inhibiting compound) with the amount of signal obtained in the presence of a possible inhibitor, it can be determined whether a possible inhibitor indeed has inhibitory capabilities or not. If the signal of the incubation of the first labelled compound (bound to the F-box protein or a functional part and/or equivalent thereof) in the absence of a possible inhibitor and in the presence of the inhibitor are approximately the same, the inhibitor will not be useful for further uses. However, if the signal obtained in the presence of a possible inhibitor is (much) lower compared to the signal obtained in the absence of the inhibitor, a possible useful inhibitor is identified.

Preferably, a method for selecting an inhibitor as described above further comprises immobilising the F-box protein or a functional part and/or equivalent thereof. This enables an easy separation of bound and unbound first labelled compound, for example, by performing one or multiple washing step(s). Suitable, non-limiting, matrices for immobilisation of the F-box protein are ELISA plates, membranes, arrays and other solid-phase-based media.

Instead of using a first labelled compound comprising at least a proteinaceous part comprising the amino acid sequence xDSWxEFIxxD (SEQ ID NO:3) or a sequence essentially corresponding thereto, it is clear that a method for selecting an inhibitor capable of inhibiting the interaction of an F-box protein with the ubiquitin/proteasome binding site/UbE motif is equally well performed with a labelled F-box protein or a functional part and/or equivalent thereof. Thus, the invention also provides a method for selecting an inhibitor capable of inhibiting the interaction of an F-box protein with a ubiquitin/proteasome binding site, comprising the steps of: contacting, in the absence or presence of a possible inhibitor, the ubiquitin/proteasome binding site (or preferably the UbE motif) comprising the amino acid sequence xDSWxEFIxxD (SEQ ID NO:3) or a sequence essentially corresponding thereto with a first labelled compound comprising the F-box protein or a functional part and/or equivalent thereof; determining the amount of the first labelled compound bound to the ubiquitin/proteasome binding site in the presence or absence of the inhibitor and comparing the obtained amounts; and selecting the inhibitor that results in a decreased amount of the bound first labelled compound.

Useful labels for the F-box protein or a functional part and/or equivalent thereof are outlined above. In a preferred embodiment, the F-box protein is β-TrCP and the functional part of the F-box protein comprises the WD40 domain. In a more preferred embodiment, the β-TrCP is β-TrCP1 and, in an even more preferred embodiment, the β-TrCP1 is β-TrCP1 variant 1.

Again, different combinations of the first labelled compound and a ubiquitin/proteasome binding site can be used. Non-limiting examples include (i) the use of a labelled, essentially complete, F-box protein as a first labelled compound in combination with a compound comprising the amino acid sequence xDSWxEFIxxD (SEQ ID NO:3) (or a sequence essentially corresponding thereto), possibly extended by a limited (two to three) amount of amino acids on the N- and/or C-terminus or (ii) the use of a labelled, essentially complete, F-box protein as a first labelled compound in combination with a compound essentially comprising the complete intracellular domain of, for example, GHR or essentially comprising the complete GHR molecule or (iii) the use of a functional part and/or equivalent of an F-box protein (for example, the WD40 domain of β-TrCP) as a first labelled compound in combination with a compound comprising only the amino acid sequence xDSWxEFIxxD (SEQ ID NO:3) (or a sequence essentially corresponding thereto), possibly extended by a limited (two to three) amount of amino acids on the N- and/or C-terminus.

Preferably, such a method further comprises immobilising the (compound comprising a) ubiquitin/proteasome binding site.

Preferably, the selected inhibitor does not interfere with other processes in which, for example, the β-TrCP molecule is also involved and, hence, the method for selecting an inhibitor capable of inhibiting the interaction of an F-box protein with a ubiquitin/proteasome binding step further comprises: contacting, in the absence or presence of the selected inhibitor, the F-box protein or a functional part and/or equivalent thereof with a second labelled compound comprising at least a proteinaceous part comprising the amino acid sequence DSGIHS (SEQ ID NO:10) or a sequence essentially corresponding thereto; determining the amount of the second labelled compound bound to the F-box protein in the presence or absence of the inhibitor and comparing the obtained amounts; and selecting the inhibitor that does not (or hardly) change(s) the amount of the second labelled compound bound to the F-box protein.

Examples of useful labels are the same as the labels described for the first labelled compound.

Selected inhibitors are optionally further tested in a cell-based assay or in an animal model for their effectiveness/usefulness.

The selected inhibitors can optionally be modified, for example, by providing the inhibitor with a means to (more efficiently) cross the cell membrane.

The invention further provides an inhibitor obtainable by a method according to the invention. Such an inhibitor may be proteinaceous or chemical, synthetically produced or obtained via recombinant techniques. Such an inhibitor may further be provided with a means to increase the inhibitor's potential to cross the cell membrane. Such inhibitors are also useful in the design of a mimetic.

The invention further provides a pharmaceutical composition comprising an inhibitor according to the invention. Such a pharmaceutical composition is, for example, useful in treating patients with hormone (e.g., growth hormone) deficiencies.

The invention also provides use of an inhibitor according to the invention for the manufacture of a medicament for treating diseases related to the availability (presence) of a cell surface receptor. More in particular, the invention provides use of an inhibitor according to the invention for the manufacture of a medicament for the treatment of (diseases that involve) cachexia. Even more in particular, the invention provides use of an inhibitor according to the invention for the manufacture of a medicament for the treatment of diseases that involve cachexia, wherein cachexia is a result of cancer, AIDS, renal insufficiency, burns or bed-ridden situations. Yet another example of use of a pharmaceutical composition provided by the invention is for the treatment of patients that are suffering from (muscle) wasting that results from increased (muscle) protein degradation that is often seen after or during disorders such as renal tubular defects, uraemia, diabetes, Cushing's syndrome, cachexias seen with cancer or with eating disorders, after serious burns, during sepsis or AIDS, after stress, during and after immobilisation, during neuromuscular disease, and other conditions that alter protein degradation in cells such as muscle cells. Experimental animal models are available to study these and other related disorders. One can, for instance, use rats to study fasting, metabolic acidosis, kidney failure, muscle denervation, diabetes, thermal injury, endotoxaemia, bacteraemia, tumour development, glucocorticoid or thyroid hormone treatment and hyperthyroidism. Studies of such experimental models have indicated that the ubiquitin/proteasome pathway is activated in muscle and causes the loss of muscle mass (wasting) in these disorders.

Yet another embodiment of the invention is a pharmaceutical composition comprising an inhibitor provided by the invention, which composition is administered in conjunction with a hormone. "In conjunction" herein means that the composition is used or applied before, during or after hormonal treatment and up-regulates or modifies the activity of the hormone.

The invention also provides for optimalisation of physical and mental condition in healthy individuals to increase lean body mass and diminish body fat without the use of GH. A selected inhibitor that is derived from a naturally occurring product is used as a dietary supplement. Such a supplement preferably has a positive effect on the properties of muscles and/or reduces the amount of fat.

The invention further provides means and methods for the treatment of acromegaly. Acromegaly is a hormonal disorder that most commonly occurs in middle-aged men and women. The name "acromegaly" comes from the Greek words for "extremities" (acro) and "great" (megaly), because one of the most common symptoms of this condition is abnormal growth of the hands and feet.

The symptoms of acromegaly can vary and they develop gradually over time; therefore, a diagnosis of this condition may be difficult. Early detection is a goal in the management of acromegaly because the pathologic effects of increased growth hormone (GH) production are progressive. Because we now know that β-TrCP interacts with the ubiquitin/proteasome binding site of GHR, β-TrCP can now be modified to be more active, i.e., increase of the cellular concentration of β-TrCP (for example, by increasing expression or by a decreased degradation). In a more preferred embodiment, the β-TrCP is β-TrCP1 and, in an even more preferred embodiment, the β-TrCP1 is β-TrCP1 variant 1.

The invention will be explained in more detail in the following description, which is non-limiting of the invention.

Materials and Methods

Materials

TrCP1 and TrCP2 cDNA in pcDNA1 expressing the flag-tagged proteins were generous gifts of Tomoki Chiba, Tokyo Metropolitan Institute of Medical Science. Full-length rabbit GHR cDNA in pcDNA3 was described (Strous et al., 1996). GST fusion proteins expressing GST-GHR (271-334), GST-GHR (271-334) F327A, and GST-GHR (271-318) were produced as described (Schantl et al., 2003). pcDNA3-GHR constructs used for alanine scanning of the UbE motif were constructed as described in Govers et al. (1999). Chemically synthesised siRNA duplexes to silence both β-TrCP1 and -2, GUG-GAAUUUGUGGAACAUCtt (SEQ ID NO:11), and GAUG-UUCCACAAAUUCCACtt (SEQ ID NO:12), and a control siRNA designed for GFP silencing were purchased from Ambion, Austin, Tex. Antibody, recognising the cytoplasmic domain of the GHR, was raised against amino acids 271-318 of the cytosolic tail of the GHR (van Kerkhof et al., 2000). Antibody (mAb5) directed against the extracellular domain of the GHR was from Amgen, Inc., Thousand Oaks, Calif. Mouse monoclonal anti-FLAG (M2) were from Sigma-Aldrich, St. Louis, Mo. MG132 (carbobenzoxy-L-leucyl-L-leucyl-L-leucinal) was purchased from Fisher Scientific Calbiochem-Novabiochem Corp., San Diego, Calif., cycloheximide was purchased from ING Biomedicals Inc. Culture media, fetal calf serum (FCS), L-glutamine, and antibiotics for tissue culture were purchased from GIBCO® cell cultures of Invitrogen, Carlsbad, Calif.

Cell Culture

Hek293 cells were grown in DMEM (Invitrogen) supplemented with 10% FCS, 100 units/ml Penicillin and 100 µg/ml streptomycin. Hek293 cells stably expressing the wtGHR (Hek-wtGHR) were grown as in the same medium supplemented with 600 µg/ml GENETICIN® (G418; Invitrogen). All cells used were grown at 37° C. with 5.0% $CO_2$ in 25 $cm^2$ or 75 $cm^2$ culture flasks. Once or twice a week, the cells were washed with phosphate-buffered saline (PBS), detached from the flask with Trypsin-EDTA (Invitrogen), diluted in fresh growth medium and split into new culture flasks. Growth medium was refreshed twice a week.

Transfections

Hek293 cells were transfected using FUGENE®6 (Roche Applied Science). Fifty percent of the confluent cultures were transfected with 0.2 µg-0.9 µg DNA in 12-well plates according to manufacturer's protocol. Transfected cells were used for Western blot experiments and for $^{125}$I-GH binding experiments one to two days after transfection.

To silence the expression of both β-TrCP1 and β-TrCP2, Hek-wtGHR cells were transfected with small interfering RNA (siRNA) using LIPOFECTAMIN® 2000 according to the description of the manufacturer; three days after transfection, the cells were used for Western blotting and $^{125}$I-GH binding experiments. Control cells were transfected with siRNA-GFP. To control the effect of the gene expression silencing, Hek293 cells were transiently transfected with a pcDNA3-TrCP construct expressing FLAG-tagged TrCP. Western-blotting using anti-Flag-tag antibody showed that less than 5% of TrCP was present in cells treated with the control siRNA.

$^{125}$I-GH Binding in Internalisation $^{125}$I-Human GH was prepared using chloramine T (Strous et al., 1996). For internalisation experiments, cells grown in 12-well plates were washed with 1 ml MEM supplemented with 20 mM Hepes, pH 7.4 and 0.1% bovine serum albumin (BSA), and incubated at 37° C. in a water bath for one hour. After washing the cells three times with ice-cold PBS-complete (PBS with 0.135 g/l $CaCl_2$ and 0.1 g/l $MgCl_2$), 750 µl $^{125}$I-GH (180 ng/ml in Mem/Hepes/0.1% BSA) was added to the cells. $^{125}$I-GH was bound for two hours on ice. Unbound $^{125}$I-GH was aspirated and the cells were washed three times with PBS-complete. Cells were incubated 0 to 10 minutes at 37° C. in MEM/Hepes/0.1% BSA to allow receptor internalisation. Cells were washed three times with ice-cold PBS-complete and membrane-associated $^{125}$I-GH was removed by treating the cells twice with 750 µl acid wash (0.15 M NaCl, 50 mM glycine, 0.1% BSA, pH 2.5) for 5 minutes on ice. Acid wash is collected in counting tubes and radioactivity was measured using an LKB gamma counter. Acid wash-treated cells were solubilised overnight in 1 N NaOH. Internalised $^{125}$I-GH was determined by measuring the radioactivity in the collected NaOH. Unspecific counts were determined by incubating the cells with $^{125}$I-GH together with excess unlabelled GH (9 µg/ml). Internalisation is expressed as a percentage of total specific radioactivity associated with the cells at 10 minutes at 37° C.

In Vitro Binding Assay

Wild-type and mutant GHR proteins were expressed in Hek293, the cells were lysed in 50 mM Tris HCl (pH 7.5), 1 M NaCl, 50 mM NaF, and 0.5% Nonidet P-40 and the receptors were purified with biotinylated GH and streptavidin beads, stringently washed with lysis buffer. The beads were incubated with in vitro-translated- and $^{35}$S-labelled-TrCP2 for 60 minutes at 4° C. The beads were extensively washed with lysis buffer, and associated proteins were analysed by sodium dodecyl sulfate-polyacrylamide gel electrophoresis (SDS-PAGE) and autoradiography. cDNA of β-TrCP2 constructs in pcDNA3.1/FLAG was used in an in vitro transcription translation system supplemented with [$^{35}$S]methionine and TNT®-T7-coupled reticulocyte lysate ready reaction mix according to the instructions of the manufacturer (Promega Corp., Madison, Wis.). Binding to GHR1-286 was taken as background.

Results

The Involvement of β-TrCP in the Endocytosis of the GHR

Figure 1:
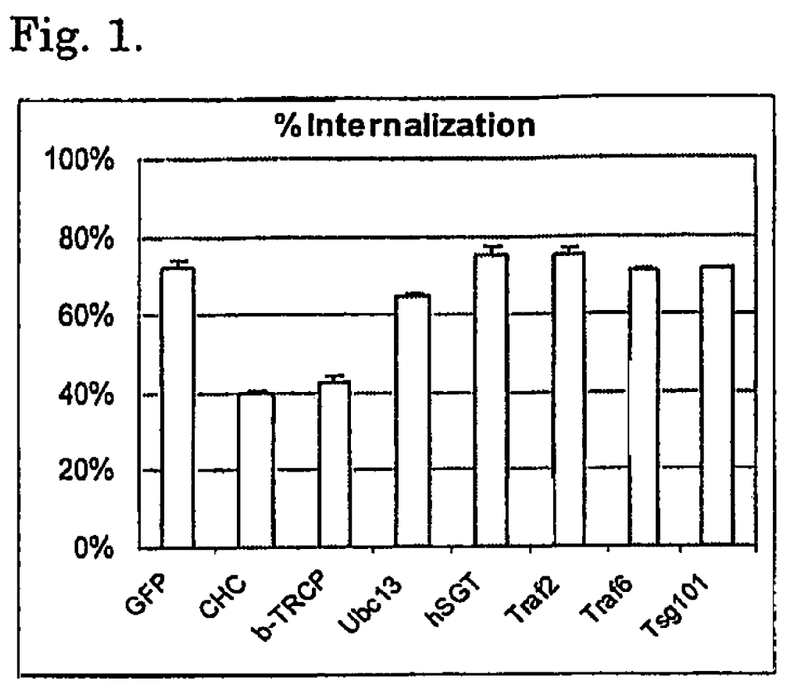

In a first experiment, the role of β-TrCP in the endocytosis of the GHR was investigated. A Hek293 cell line expressing the rabbit GHR was transfected with siRNA for three days, and uptake of $^{125}$I-GH was measured for 10 minutes. As a negative control, the expression of clathrin was silenced (CHC); in another control, siRNA for green fluorescent protein was used (GFP). As seen in FIG. 1, siRNA for β-TrCP inhibits GH uptake to the same extent as siRNA(CHC), approximately 50% as compared to non-relevant siRNA (GFP). Silencing of various other genes, like the E2 Ubc13, the RING E3s Traf2 and Traf6, and the endosomal cargo selector complex ESCRT2 protein TSG101, did not affect GH uptake.

We conclude that β-TrCP is involved in endocytosis of the GHR.

Mutational Analysis of the UbE Motif

Previously, we have shown that endocytosis of the GHR depends both on a functional ubiquitination system and on an intact UbE motif (Govers et al., 1997; Strous et al., 1996; van Kerkhof et al., 2002). Using mutational analysis of the UbE motif by changing every single amino acid residue into alanine, the contribution of each amino acid was determined. The experiment showed that mutation of some of the residues, indicated in bold (and underlined) in the UbE motif (DDSWV EFIELD) (SEQ ID NO:1) almost completely inhibited endocytosis. As shown in FIG. 1, β-TrCP acts as a regulator of GHR endocytosis. We used a pull-down assay to ask whether β-TrCP binds to the GHR in a specific fashion. Hek293 cells were transfected with 15 GHR constructs in which each of the amino acids of the UbE motif were changed into alanine (NDDSWVEFIELDIDD (SEQ ID NO:7), 320-334). After 24 hours, the GH-GHR complexes were isolated and incubated with equal amounts of β-TrCP, $^{35}$S-labelled in an in vitro transcription-translation system. The bound radioactivity was analysed by electrophoresis on SDS gels and quantitated. As a control, DNA encoding wild-type GHR (FIG. 2, wtGHR) was used, and as a negative control, DNA encoding GHR truncated at amino acid 286 (FIG. 2, 286), lacking the UbE motif, was used. The results show that except for the N320A, every mutation resulted in inhibition of β-TrCP binding as compared to wtGHR. However, mutation of seven amino acids inhibited the β-TrCP binding with more than 60% indicated as underlined (DDSWVEFIELD) (SEQ ID NO:1), while the greatest effects were observed if either one of three acidic amino acid residues (D321, E326, D331) or S323, or W324 were mutated into alanine. The latter effects approximated the background signal measured for the GHR truncated at amino acid 286. No binding was observed for the DSGRTS (SEQ ID NO:15) motif at position 365 (not shown). Further domain analysis using mutations and deletions of β-TrCP showed that the interaction between the UbE motif and β-TrCP occurs via its WD40 domain (not shown).

From comparison between the mutational analyses previously measured for GHR endocytosis and the results obtained with the same constructs for GHR-β-TrCP interaction, we conclude that β-TrCP is a prime regulator of GHR endocytosis via the UbE motif (DDSWVEFIELD (SEQ ID NO:1)).

Previously, we have shown that GHR endocytosis and subsequent degradation in the lysosomes depend on the activity of the ubiquitin system via the UbE motif. Here, we identify β-TrCP as the factor that is required for GHR endocytosis by gene silencing and that β-TrCP specifically binds to the GHR at the same motif as required for ubiquitination-dependent endocytosis. These data support the conclusion that this factor recruits the ubiquitination machinery. Whether the complete SCF(β-TrCP) complex including skp1, cul1, rbx1, and an E2 conjugase is present at the GHR tail, remains to be determined.

The interaction between β-TrCP and the UbE motif is via the WD40 domain. Detailed structural information is available on the interaction between the WD40 domain of the SCF(β-TrCP) with β-catenin (Wu et al., 2003). The F-box protein β-TrCP recognises the doubly phosphorylated DpS-GΦXpS destruction motif present in β-catenin, and directs the SCF(β-TrCP) E3 to ubiquitinate it at a lysine residue 13 amino acids upstream of the destruction motif (the lysine residue is commonly present at the 9-14 positions upstream). The β-catenin peptide binds the top face of the β-propeller, with the six-residue destruction motif dipping into the central channel. The middle portion of the peptide has an extended conformation, and the two ends have turn-like conformations. All seven WD40 repeats of β-TrCP contribute contacts to β-catenin. Comparison with the UbE motif reveals little resemblance to the catenin destruction motif: the UbE motif is 11 amino acids long, it contains three acidic residues critical for binding (D321, E326, D331) instead of the two phosphorylated serine residues in β-catenin, and lacks a glycine residue present in all phosphorylated DSGΦXS destruction motifs described until now (Fuchs et al., 2004; Kanemori et al., 2005). Another deviation is the lack of a lysine residue at 9-14 positions upstream, although there is a conserved lysine at position 315 immediately after a tyrosine that is phosphorylated upon GH binding. However, mutation of this lysine residue into arginine does not affect the half-life of the GHR, nor its ubiquitination-dependent endocytosis behaviour (Govers et al., 1999). Together, these results are in line with our previous observation that ubiquitination of the GHR is not required for endocytosis. Thus, binding of a presumed SCF (β-TrCP) E3 does not target the GHR for ubiquitination but is probably directed toward another factor in the GHR-ubiquitination complex (Govers et al., 1999). Before three-dimensional (3D) scanning will reveal the precise interaction between the β-TrCP-WD40 domain and the UbE motif, it is already clear that the UbE-WD40 interaction differs considerably from the WD40-DSGΦXS destruction motif interactions described until now.

Interaction of β-TrCP is the first step toward factual endocytosis of the GHR via a clathrin-mediated selection process. To involve the ubiquitination machinery in this process, the GHR must be dimerised (Gent et al., 2002).

Recent observations of β-TrCP show that it indeed contains a dimerisation domain that is important for its E3 function (Suzuki et al., 2000). Our in vitro binding experiments with GST-GHR tails reveal that monomeric GHR can bind β-TrCP. It remains to be investigated whether the dimerisation of β-TrCP poses the necessity for dimerisation on the GHR.

Cargo selection via β-TrCP thus requires an active E3, followed by proteasomal activity, and interaction with the clathrin-mediated machinery (Govers et al., 1999). Whether the full SCF(β-TrCP) E3 is in place to ubiquitinate factor X and enable GHR to connect to the propeller structure of the clathrin heavy chain, remains open. Previously, we have identified several factors that bound specifically to the UbE motif (Schantl et al., 2003). The tetratricopeptide repeat-containing protein SGT might be a factor bridging the gap between TrCP and clathrin via the U-box ligase carboxyl-terminus of Hsc 70-interacting protein (CHIP) (Schantl et al., 2003; Timsit et al., 2005).

β-TrCP is a factor in the degradation of prolactin and interferon receptors (Kumar et al., 2003; Kumar et al., 2004; Li et al., 2004). Fuchs et al. identified β-TrCP to act upon and interact with these receptors via their DSGΦXS destruction motifs. They also show that SCF(β-TrCP2) E3 ubiquitinates both the interferon-α and prolactin receptors, dependent on an intact DSGΦXS motif. The assumption is that upon ligand binding (interferon-α and prolactin), this motif is phosphorylated by a yet unidentified kinase after which the SCF(β-TrCP2) E3 ubiquitinates certain lysines in the tails of the receptors. This leads to their destruction. It is clear that this scenario differs from how β-TrCP is involved in GHR endocytosis. Although the GHR contains a DSGRTS (SEQ ID NO:15) sequence, reminiscent to the DSGΦXS destruction motifs, mutation of the serine residues did not result in a shorter half-life nor in inhibition of the endocytosis of the GHR (unpublished). It is tempting to speculate that this sequence is involved in down-stream events originating from the action of γ-secretase on the GHR tail (Cowan et al., 2005).

Ubiquitination by the SCF(β-TrCP) E3 of a factor generally results in its destruction by the proteasome. In most cases, the decision to degrade the target is not in the SCF(β-TrCP) E3 action, but rather due to the activity of one or two kinases that phosphorylate the serine residues in the degradation motif. Our experiments with GST-GHR fusion proteins indicate that binding of β-TrCP to the UbE motif does not depend on a preceding action of another post-translation modification. Thus, very likely, the cytosolic concentration of β-TrCP determines its activity level to induce GHR endocytosis. This is reflected in the experiment in FIG. 1 that shows that decreased amounts of β-TrCP inhibit GH and GHR uptake. Thus, the cytosolic concentration of β-TrCP may function as a factor in GH sensitivity of cells: at low concentrations, the cells are more sensitive to GH than at high concentrations. This immediately raises the question: what determines the cellular concentration of β-TrCP? Generally, β-TrCP is part of an E3 complex that is involved in degradation of key factors controlling cell growth, survival and transformation (Fuchs et al., 2004). As it is a short-lived protein itself, more studies are needed to understand the consequences of β-TrCP concentrations for cellular regulation, and the GHR activity in particular.

REFERENCES

Cowan J. W., X. Wang, R. Guan, K. He, J. Jiang, G. Baumann, R. A. Black, M. S. Wolfe, and S. J. Frank (2005). Growth Hormone Receptor is a Target for Presenilin-dependent γ-Secretase Cleavage. *J. Biol. Chem.* 280:19331-19342.

Fuchs S. Y., V. S. Spiegelman, and K. G. Kumar (2004). The many faces of β-TrCP E3 ubiquitin ligases: reflections in the magic mirror of cancer. *Oncogene* 23:2028-2036.

Galan J. M. and R. Haguenauer-Tsapis (1997). Ubiquitin Lys63 is involved in ubiquitination of a yeast plasma membrane protein. *EMBO. Journal* 16:5847-5854.

Gent J., P. van Kerkhof, M. Roza, G. Bu, and G. J. Strous (2002). Ligand-independent growth hormone receptor dimerisation occurs in the endoplasmic reticulum and is required for ubiquitin system-dependent endocytosis. *Proc. Nat. Acad. Sci. U.S.A.* 99:9858-9863.

Govers R., T. ten Broeke, P. van Kerkhof, A. L. Schwartz, and G. J. Strous (1999). Identification of a novel ubiquitin conjugation motif, required for ligand-induced internalisation of the growth hormone receptor. *EMBO. J.* 18:28-36.

Govers R., P. van Kerkhof, A. L. Schwartz, and G. J. Strous (1997). Linkage of the ubiquitin-conjugating system and the endocytic pathway in ligand-induced internalisation of the growth hormone receptor. *EMBO. J.* 16:4851-4858.

Hershko A., A. Ciechanover, and A. Varshaysky (2000). Basic Medical Research Award. The ubiquitin system. *Nat. Med.* 6:1073-1081.

Hicke L. and R. Dunn (2003). Regulation of membrane protein transport by ubiquitin and ubiquitin-binding proteins. *Annu. Rev. Cell. Dev. Biol.* 19:141-172.

Kanemori Y., K. Uto, and N. Sagata (2005). β-TrCP recognises a previously undescribed nonphosphorylated destruction motif in Cdc25A and Cdc25B phosphatases. *PNAS* 102:6279-6284.

Kumar K. G., W. Tang, A. K. Ravindranath, W. A. Clark, E. Croze, and S. Y. Fuchs (2003). SCF(HOS) ubiquitin ligase mediates the ligand-induced down-regulation of the interferon-α receptor. *EMBO. J.* 22:5480-5490.

Kumar K. G. S., J. J. Krolewski, and S. Y. Fuchs (2004). Phosphorylation and Specific Ubiquitin Acceptor Sites are Required for Ubiquitination and Degradation of the IFNAR1 Subunit of Type I Interferon Receptor. *J. Biol. Chem.* 279:46614-46620.

Li Y., K. G. Suresh Kumar, W. Tang, V. S. Spiegelman, and S. Y. Fuchs (2004). Negative Regulation of Prolactin Receptor Stability and Signalling Mediated by SCF(β-TrCP) E3 Ubiquitin Ligase. *Mol. Cell. Biol.* 24:4038-4048.

Plemper R. K. and D. H. Wolf (1999). Retrograde protein translocation: ERADication of secretory proteins in health and disease. *Tr. Biochem. Sci.* 24:266-270.

Roth A. F. and N. G. Davis (2000). Ubiquitination of the PEST-like endocytosis signal of the yeast a-factor receptor. *Journal of Biological Chemistry* 275:8143-8153.

Schantl J. A., M. Roza, A. P. de Jong, and G. J. Strous (2003). Small glutamine-rich tetratricopeptide repeat-containing protein interacts with the ubiquitin-dependent endocytosis motif of the growth hormone receptor. *Biochem. J.* 373: 855-863.

Shenoy S. K., P. H. McDonald, T. A. Kohout, and R. J. Lefkowitz (2001). Regulation of Receptor Fate by Ubiquitination of Activated β2-Adrenergic Receptor and β-Arrestin. *Science* 294:1307-1313.

Staub O., I. Gautschi, T. Ishikawa, K. Breitschopf, A. Ciechanover, L. Schild, and D. Rotin (1997). Regulation of stability and function of the epithelial Na$^+$ channel (ENaC) by ubiquitination. *EMBO. J.* 16:6325-6336.

Strous G. and J. Gent (2002). Dimerisation, ubiquitylation and endocytosis go together in growth hormone receptor function. *FEBS. Lett.* 529:102-109.

Strous G. J. and R. Govers (1999). The ubiquitin-proteasome system and endocytosis. *J. Cell Science* 112:1417-1423.

Strous G. J., P. van Kerkhof, R. Govers, A. Ciechanover, and A. L. Schwartz (1996). The ubiquitin conjugation system is required for ligand-induced endocytosis and degradation of the growth hormone receptor. *EMBO. J.* 15:3806-3812.

Suzuki H., T. Chiba, T. Suzuki, T. Fujita, T. Ikenoue, M. Omata, K. Furuichi, H. Shikama, and K. Tanaka (2000). Homodimer of two F-box proteins β-TrCP1 or β-TrCP2 binds to IκBα for signal-dependent ubiquitination. *Journal of Biological Chemistry* 275:2877-2884.

Terrell J., S. Shih, R. Dunn, and L. Hicke (1998). A function for monoubiquitination in the internalisation of a G protein-coupled receptor. *Mol. Cell.* 1:193-202.

Timsit Y. E., S. L. Miller, R. P. Mohney, and J. P. O'Bryan (2005). The U-box ligase carboxyl-terminus of Hsc 70-interacting protein ubiquitylates Epsin. *Biochem. Biophys. Res. Commun.* 328:550-559.

van Kerkhof P., M. Smeets, and G. J. Strous (2002). The Ubiquitin-Proteasome Pathway Regulates the Availability of the GH Receptor. *Endocrinology* 143:1243-1252.

van Kerkhof P., E. Vallon, and G. J. Strous (2003). A method to increase the number of growth hormone receptors at the surface of cells. *Mol. Cell. Endocrinol.* 201:57-62.

Wu G., G. Xu, B. A. Schulman, P. D. Jeffrey, J. W. Harper, and N. P. Pavletich (2003). Structure of a β-TrCP1-Skp1-β-catenin complex: destruction motif binding and lysine specificity of the SCF(β-TrCP1) ubiquitin ligase. *Mol. Cell.* 11:1445-1456.

The invention claimed is:

1. A method for interfering with the interaction of a β-TrCP with a ubiquitin/proteasome binding site of growth hormone receptor on a cell, the method comprising:
    administering, to the cell, an inhibitor for interfering with the interaction of a β-TrCP with a ubiquitin/proteasome binding site of the growth hormone receptor;
    wherein said ubiquitin/proteasome binding site comprises the amino acid sequence motif xDSWxEFIxxD (SEQ ID NO:3); and
    wherein said inhibitor is a β-TrCP siRNA or a polypeptide comprising the amino acid sequence motif xDSWxEFIxxD (SEQ ID NO:3).

2. The method according to claim 1, wherein said β-TrCP is β-TrCP1.

3. The method according to claim 2, wherein said β-TrCP1 is β-TrCP1 variant 1.

4. The method according to claim 1, wherein said ubiquitin/proteasome binding site comprises the amino acid sequence motif DDSWVEFIELD (SEQ ID NO:1) or a sequence essentially corresponding thereto.

5. A method of inhibiting growth hormone receptor endocytosis in an individual, comprising administering to an individual in need thereof an effective amount of an inhibitor for interfering with the interaction of β-TrCP with a ubiquitin/proteasome binding site of growth hormone receptor wherein said ubiquitin/proteasome binding site comprises the amino acid sequence motif xDSWxEFIxxD (SEQ ID NO:3) and wherein said inhibitor is a β-TrCP siRNA or a polypeptide comprising the amino acid sequence motif xDSWxEFIxxD (SEQ ID NO:3).

* * * * *

SEQUENCE LISTING

```
<160> NUMBER OF SEQ ID NOS: 15

<210> SEQ ID NO 1
<211> LENGTH: 11
<212> TYPE: PRT
<213> ORGANISM: Artificial Sequence
<220> FEATURE:
<223> OTHER INFORMATION: Ubiquitin-dependent endocytosis motif
      (UbE-motif)

<400> SEQUENCE: 1

Asp Asp Ser Trp Val Glu Phe Ile Glu Leu Asp
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Substrate binding motif
<220> FEATURE:
<221> NAME/KEY: MISC_FEATURE
<222> LOCATION: (4)..(5)
```

```
<223> OTHER INFORMATION: "Xaa" at pos. 4 and 5 stands for any amino
      acid

<400> SEQUENCE: 2

Asp Ser Gly Xaa Xaa Ser
1               5

<210> SEQ ID NO 3
<211> LENGTH: 11
<212> TYPE: PRT
<213> ORGANISM: Artificial Sequence
<220> FEATURE:
<223> OTHER INFORMATION: Ubiquitin/proteasome binding site
<220> FEATURE:
<221> NAME/KEY: MISC_FEATURE
<222> LOCATION: (1)..(10)
<223> OTHER INFORMATION: "Xaa" at pos. 1, 5, 9, and 10 stands for any
      amino acid

<400> SEQUENCE: 3

Xaa Asp Ser Trp Xaa Glu Phe Ile Xaa Xaa Asp
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Ubiquitin/proteasome binding site
<220> FEATURE:
<221> NAME/KEY: MISC_FEATURE
<222> LOCATION: (2)..(10)
<223> OTHER INFORMATION: "Xaa" at pos. 2, 5, 9, and 10 stands for any
      amino acid

<400> SEQUENCE: 4

Asp Xaa Ser Trp Xaa Glu Phe Ile Xaa Xaa Asp
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Ubiquitin/proteasome binding site
<220> FEATURE:
<221> NAME/KEY: MISC_FEATURE
<222> LOCATION: (5)..(10)
<223> OTHER INFORMATION: "Xaa" at pos. 5, 9, and 10 stands for any
      amino acid

<400> SEQUENCE: 5

Asp Asp Ser Trp Xaa Glu Phe Ile Xaa Xaa Asp
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Ubiquitin/proteasome binding site

<400> SEQUENCE: 6

Asp Asp Ser Trp Val Glu Phe Ile Glu Leu Asp Ile
1               5                   10

<210> SEQ ID NO 7
<211> LENGTH: 15
<212> TYPE: PRT
<213> ORGANISM: Artificial Sequence
```

```
<220> FEATURE:
<223> OTHER INFORMATION: Ubiquitin/proteasome binding site

<400> SEQUENCE: 7

Asn Asp Asp Ser Trp Val Glu Phe Ile Glu Leu Asp Ile Asp Asp
1               5                   10                  15

<210> SEQ ID NO 8
<211> LENGTH: 61
<212> TYPE: PRT
<213> ORGANISM: Artificial Sequence
<220> FEATURE:
<223> OTHER INFORMATION: Peptide consisting of amino acids 270-331 of
      human GHR

<400> SEQUENCE: 8

Lys Gln Gln Arg Ile Lys Met Leu Ile Leu Pro Pro Val Pro Val Pro
1               5                   10                  15

Lys Ile Lys Gly Ile Asp Pro Asp Leu Leu Lys Glu Gly Lys Leu Glu
                20                  25                  30

Glu Val Asn Thr Ile Leu Ala Ile His Asp Ser Tyr Lys Pro Glu Phe
            35                  40                  45

His Ser Asp Asp Ser Trp Val Glu Phe Ile Glu Leu Asp
        50                  55                  60

<210> SEQ ID NO 9
<211> LENGTH: 61
<212> TYPE: PRT
<213> ORGANISM: Artificial Sequence
<220> FEATURE:
<223> OTHER INFORMATION: Peptide consisting of 61 amino acids from
      rabbit GHR

<400> SEQUENCE: 9

Lys Gln Gln Arg Ile Lys Met Leu Ile Leu Pro Pro Val Pro Val Pro
1               5                   10                  15

Lys Ile Lys Gly Ile Asp Pro Asp Leu Leu Lys Glu Gly Lys Leu Glu
                20                  25                  30

Glu Val Asn Thr Ile Leu Ala Ile Gln Asp Ser Tyr Lys Pro Glu Phe
            35                  40                  45

Tyr Asn Asp Asp Ser Trp Val Glu Phe Ile Glu Leu Asp
        50                  55                  60

<210> SEQ ID NO 10
<211> LENGTH: 6
<212> TYPE: PRT
<213> ORGANISM: Artificial Sequence
<220> FEATURE:
<223> OTHER INFORMATION: Proteinaceous part of labelled compound

<400> SEQUENCE: 10

Asp Ser Gly Ile His Ser
1               5

<210> SEQ ID NO 11
<211> LENGTH: 19
<212> TYPE: RNA
<213> ORGANISM: Artificial Sequence
<220> FEATURE:
<223> OTHER INFORMATION: siRNA duplex to beta-TrCP1

<400> SEQUENCE: 11
guggaauuug uggaacauc                                                    19
```

```
<210> SEQ ID NO 12
<211> LENGTH: 19
<212> TYPE: RNA
<213> ORGANISM: Artificial Sequence
<220> FEATURE:
<223> OTHER INFORMATION: siRNA duplex to beta-TrCP2

<400> SEQUENCE: 12
gauguuccac aaauuccac                                                  19

<210> SEQ ID NO 13
<211> LENGTH: 605
<212> TYPE: PRT
<213> ORGANISM: Homo sapiens

<400> SEQUENCE: 13
```

Met Asp Pro Ala Glu Ala Val Leu Gln Glu Lys Ala Leu Lys Phe Met
1               5                   10                  15

Cys Ser Met Pro Arg Ser Leu Trp Leu Gly Cys Ser Ser Leu Ala Asp
            20                  25                  30

Ser Met Pro Ser Leu Arg Cys Leu Tyr Asn Pro Gly Thr Gly Ala Leu
        35                  40                  45

Thr Ala Phe Gln Asn Ser Ser Glu Arg Glu Asp Cys Asn Asn Gly Glu
    50                  55                  60

Pro Pro Arg Lys Ile Ile Pro Glu Lys Asn Ser Leu Arg Gln Thr Tyr
65                  70                  75                  80

Asn Ser Cys Ala Arg Leu Cys Leu Asn Gln Glu Thr Val Cys Leu Ala
                85                  90                  95

Ser Thr Ala Met Lys Thr Glu Asn Cys Val Ala Lys Thr Lys Leu Ala
            100                 105                 110

Asn Gly Thr Ser Ser Met Ile Val Pro Lys Gln Arg Lys Leu Ser Ala
        115                 120                 125

Ser Tyr Glu Lys Glu Lys Glu Leu Cys Val Lys Tyr Phe Glu Gln Trp
    130                 135                 140

Ser Glu Ser Asp Gln Val Glu Phe Val Glu His Leu Ile Ser Gln Met
145                 150                 155                 160

Cys His Tyr Gln His Gly His Ile Asn Ser Tyr Leu Lys Pro Met Leu
                165                 170                 175

Gln Arg Asp Phe Ile Thr Ala Leu Pro Ala Arg Gly Leu Asp His Ile
            180                 185                 190

Ala Glu Asn Ile Leu Ser Tyr Leu Asp Ala Lys Ser Leu Cys Ala Ala
        195                 200                 205

Glu Leu Val Cys Lys Glu Trp Tyr Arg Val Thr Ser Asp Gly Met Leu
    210                 215                 220

Trp Lys Lys Leu Ile Glu Arg Met Val Arg Thr Asp Ser Leu Trp Arg
225                 230                 235                 240

Gly Leu Ala Glu Arg Arg Gly Trp Gly Gln Tyr Leu Phe Lys Asn Lys
                245                 250                 255

Pro Pro Asp Gly Asn Ala Pro Asn Ser Phe Tyr Arg Ala Leu Tyr
            260                 265                 270

Pro Lys Ile Ile Gln Asp Ile Glu Thr Ile Glu Ser Asn Trp Arg Cys
        275                 280                 285

Gly Arg His Ser Leu Gln Arg Ile His Cys Arg Ser Glu Thr Ser Lys
    290                 295                 300

Gly Val Tyr Cys Leu Gln Tyr Asp Asp Gln Lys Ile Val Ser Gly Leu
305                 310                 315                 320

Arg Asp Asn Thr Ile Lys Ile Trp Asp Lys Asn Thr Leu Glu Cys Lys

```
            325                 330                 335
Arg Ile Leu Thr Gly His Thr Gly Ser Val Leu Cys Leu Gln Tyr Asp
            340                 345                 350

Glu Arg Val Ile Ile Thr Gly Ser Ser Asp Ser Thr Val Arg Val Trp
            355                 360                 365

Asp Val Asn Thr Gly Glu Met Leu Asn Thr Leu Ile His His Cys Glu
            370                 375                 380

Ala Val Leu His Leu Arg Phe Asn Asn Gly Met Met Val Thr Cys Ser
385                 390                 395                 400

Lys Asp Arg Ser Ile Ala Val Trp Asp Met Ala Ser Pro Thr Asp Ile
                405                 410                 415

Thr Leu Arg Arg Val Leu Val Gly His Arg Ala Ala Val Asn Val Val
            420                 425                 430

Asp Phe Asp Asp Lys Tyr Ile Val Ser Ala Ser Gly Asp Arg Thr Ile
                435                 440                 445

Lys Val Trp Asn Thr Ser Thr Cys Glu Phe Val Arg Thr Leu Asn Gly
            450                 455                 460

His Lys Arg Gly Ile Ala Cys Leu Gln Tyr Arg Asp Arg Leu Val Val
465                 470                 475                 480

Ser Gly Ser Ser Asp Asn Thr Ile Arg Leu Trp Asp Ile Glu Cys Gly
                485                 490                 495

Ala Cys Leu Arg Val Leu Glu Gly His Glu Glu Leu Val Arg Cys Ile
            500                 505                 510

Arg Phe Asp Asn Lys Arg Ile Val Ser Gly Ala Tyr Asp Gly Lys Ile
            515                 520                 525

Lys Val Trp Asp Leu Val Ala Ala Leu Asp Pro Arg Ala Pro Ala Gly
            530                 535                 540

Thr Leu Cys Leu Arg Thr Leu Val Glu His Ser Gly Arg Val Phe Arg
545                 550                 555                 560

Leu Gln Phe Asp Glu Phe Gln Ile Val Ser Ser His Asp Asp Thr
                565                 570                 575

Ile Leu Ile Trp Asp Phe Leu Asn Asp Pro Ala Ala Gln Ala Glu Pro
            580                 585                 590

Pro Arg Ser Pro Ser Arg Thr Tyr Thr Tyr Ile Ser Arg
            595                 600                 605

<210> SEQ ID NO 14
<211> LENGTH: 569
<212> TYPE: PRT
<213> ORGANISM: Homo sapiens

<400> SEQUENCE: 14

Met Asp Pro Ala Glu Ala Val Leu Gln Glu Lys Ala Leu Lys Phe Met
1               5                   10                  15

Asn Ser Ser Glu Arg Glu Asp Cys Asn Asn Gly Glu Pro Pro Arg Lys
            20                  25                  30

Ile Ile Pro Glu Lys Asn Ser Leu Arg Gln Thr Tyr Asn Ser Cys Ala
        35                  40                  45

Arg Leu Cys Leu Asn Gln Glu Thr Val Cys Leu Ala Ser Thr Ala Met
    50                  55                  60

Lys Thr Glu Asn Cys Val Ala Lys Thr Lys Leu Ala Asn Gly Thr Ser
65                  70                  75                  80

Ser Met Ile Val Pro Lys Gln Arg Lys Leu Ser Ala Ser Tyr Glu Lys
            85                  90                  95

Glu Lys Glu Leu Cys Val Lys Tyr Phe Glu Gln Trp Ser Glu Ser Asp
```

```
                    100                 105                 110
        Gln Val Glu Phe Val Glu His Leu Ile Ser Gln Met Cys His Tyr Gln
                    115                 120                 125
        His Gly His Ile Asn Ser Tyr Leu Lys Pro Met Leu Gln Arg Asp Phe
                    130                 135                 140
        Ile Thr Ala Leu Pro Ala Arg Gly Leu Asp His Ile Ala Glu Asn Ile
        145                 150                 155                 160
        Leu Ser Tyr Leu Asp Ala Lys Ser Leu Cys Ala Ala Glu Leu Val Cys
                    165                 170                 175
        Lys Glu Trp Tyr Arg Val Thr Ser Asp Gly Met Leu Trp Lys Lys Leu
                    180                 185                 190
        Ile Glu Arg Met Val Arg Thr Asp Ser Leu Trp Arg Gly Leu Ala Glu
                    195                 200                 205
        Arg Arg Gly Trp Gly Gln Tyr Leu Phe Lys Asn Lys Pro Pro Asp Gly
                    210                 215                 220
        Asn Ala Pro Pro Asn Ser Phe Tyr Arg Ala Leu Tyr Pro Lys Ile Ile
        225                 230                 235                 240
        Gln Asp Ile Glu Thr Ile Glu Ser Asn Trp Arg Cys Gly Arg His Ser
                    245                 250                 255
        Leu Gln Arg Ile His Cys Arg Ser Glu Thr Ser Lys Gly Val Tyr Cys
                    260                 265                 270
        Leu Gln Tyr Asp Asp Gln Lys Ile Val Ser Gly Leu Arg Asp Asn Thr
                    275                 280                 285
        Ile Lys Ile Trp Asp Lys Asn Thr Leu Glu Cys Lys Arg Ile Leu Thr
                    290                 295                 300
        Gly His Thr Gly Ser Val Leu Cys Leu Gln Tyr Asp Glu Arg Val Ile
        305                 310                 315                 320
        Ile Thr Gly Ser Ser Asp Ser Thr Val Arg Val Trp Asp Val Asn Thr
                    325                 330                 335
        Gly Glu Met Leu Asn Thr Leu Ile His His Cys Glu Ala Val Leu His
                    340                 345                 350
        Leu Arg Phe Asn Asn Gly Met Met Val Thr Cys Ser Lys Asp Arg Ser
                    355                 360                 365
        Ile Ala Val Trp Asp Met Ala Ser Pro Thr Asp Ile Thr Leu Arg Arg
                    370                 375                 380
        Val Leu Val Gly His Arg Ala Ala Val Asn Val Val Asp Phe Asp Asp
        385                 390                 395                 400
        Lys Tyr Ile Val Ser Ala Ser Gly Asp Arg Thr Ile Lys Val Trp Asn
                    405                 410                 415
        Thr Ser Thr Cys Glu Phe Val Arg Thr Leu Asn Gly His Lys Arg Gly
                    420                 425                 430
        Ile Ala Cys Leu Gln Tyr Arg Asp Arg Leu Val Val Ser Gly Ser Ser
                    435                 440                 445
        Asp Asn Thr Ile Arg Leu Trp Asp Ile Glu Cys Gly Ala Cys Leu Arg
                    450                 455                 460
        Val Leu Glu Gly His Glu Glu Leu Val Arg Cys Ile Arg Phe Asp Asn
        465                 470                 475                 480
        Lys Arg Ile Val Ser Gly Ala Tyr Asp Gly Lys Ile Lys Val Trp Asp
                    485                 490                 495
        Leu Val Ala Ala Leu Asp Pro Arg Ala Pro Ala Gly Thr Leu Cys Leu
                    500                 505                 510
        Arg Thr Leu Val Glu His Ser Gly Arg Val Phe Arg Leu Gln Phe Asp
                    515                 520                 525
```

```
Glu Phe Gln Ile Val Ser Ser Ser His Asp Asp Thr Ile Leu Ile Trp
    530                 535                 540

Asp Phe Leu Asn Asp Pro Ala Ala Gln Ala Glu Pro Pro Arg Ser Pro
545                 550                 555                 560

Ser Arg Thr Tyr Thr Tyr Ile Ser Arg
                565

<210> SEQ ID NO 15
<211> LENGTH: 6
<212> TYPE: PRT
<213> ORGANISM: Artificial Sequence
<220> FEATURE:
<223> OTHER INFORMATION: Substrate binding motif

<400> SEQUENCE: 15

Asp Ser Gly Arg Thr Ser
1               5
```